United States Patent
Kishi

(10) Patent No.: US 10,575,912 B2
(45) Date of Patent: Mar. 3, 2020

(54) WIRE DRIVING DEVICE AND MANIPULATOR

(71) Applicant: OLYMPUS CORPORATION, Tokyo (JP)

(72) Inventor: Kosuke Kishi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/220,851

(22) Filed: Dec. 14, 2018

(65) Prior Publication Data

US 2019/0117325 A1    Apr. 25, 2019

Related U.S. Application Data

(63) Continuation of application No. 15/235,179, filed on Aug. 12, 2016, now Pat. No. 10,188,473, which is a
(Continued)

(30) Foreign Application Priority Data

Feb. 24, 2014 (JP) .................................. 2014-032969

(51) Int. Cl.
*A61B 34/00* (2016.01)
*F16H 9/10* (2006.01)
(Continued)

(52) U.S. Cl.
CPC ............ *A61B 34/71* (2016.02); *A61B 1/0057* (2013.01); *B25J 9/102* (2013.01); *B25J 9/104* (2013.01);
(Continued)

(58) Field of Classification Search
CPC . A61B 34/71; A61B 1/0057; A61B 2034/301; A61B 2034/715; B25J 9/104;
(Continued)

(56) References Cited

U.S. PATENT DOCUMENTS 4,137,789 A * 2/1979 Herleth ..................... F16H 3/40
                                                              74/404
4,939,607 A    7/1990 Saito
(Continued)

FOREIGN PATENT DOCUMENTS

JP         S62-148176 A    7/1987
JP         4145464 B2      9/2008
(Continued)

OTHER PUBLICATIONS

International Search Report dated Apr. 28, 2015 issued in PCT/JP2015/054958.
(Continued)

*Primary Examiner* — Bobby Rushing, Jr.
(74) *Attorney, Agent, or Firm* — Scully, Scott, Murphy & Presser, P.C.

(57) ABSTRACT

Provided is a wire driving device including: wires one ends of which are attached to a movable member; pulleys to which the other ends of the individual wires are secured; driven gears that are coaxially secured to the individual pulleys; a drive gear that is connected to a driving source; and movable gears that are disposed between the drive gear and the individual driven gears and that can transmit the motive power of the driving source to the driven gears from the drive gear. The movable gears are provided in a movable manner so that the movable gears engage with the drive gear and the driven gears when the drive gear is rotated in a direction, and so that the engagements of the movable gears with at least one of the drive gear and the driven gears are released when the drive gear is rotated in the other direction.

16 Claims, 12 Drawing Sheets

Related U.S. Application Data continuation of application No. PCT/JP2015/054958, filed on Feb. 23, 2015.

(51) Int. Cl.
| | |
|---|---|
| *F16H 3/20* | (2006.01) |
| *B25J 9/10* | (2006.01) |
| *A61B 1/005* | (2006.01) |
| *A61B 34/30* | (2016.01) |
| *F16H 3/30* | (2006.01) |
| *F16H 19/00* | (2006.01) |
| *F16H 7/08* | (2006.01) |

(52) U.S. Cl.
CPC .............. *F16H 3/20* (2013.01); *F16H 3/30* (2013.01); *F16H 9/10* (2013.01); *F16H 19/005* (2013.01); *A61B 2034/301* (2016.02); *A61B 2034/715* (2016.02); *F16H 2007/0865* (2013.01)

(58) Field of Classification Search
CPC ... B25J 9/105; B25J 9/102; F16H 3/20; F16H 3/30; F16H 9/10; F16H 2007/0865; F16H 7/22; F16H 9/125; F16H 2019/0686; F16H 55/171; F16H 2061/66295
USPC ......... 74/71, 72, 352, 490.04; 254/342, 345, 254/390
See application file for complete search history.

(56) References Cited

U.S. PATENT DOCUMENTS

| | | | | |
|---|---|---|---|---|
| 5,020,388 A | * | 6/1991 | Maeda | B25J 9/104 623/63 |
| 5,109,723 A | * | 5/1992 | Kato | G11B 15/1883 360/85 |
| 5,828,813 A | | 10/1998 | Ohm | |
| 8,490,511 B2 | * | 7/2013 | Saito | B25J 9/104 52/108 |
| 8,776,632 B2 | * | 7/2014 | Gao | B25J 9/102 254/394 |
| 8,918,023 B2 | * | 12/2014 | Nozaki | F16H 3/20 399/167 |
| 9,139,251 B2 | | 9/2015 | Maerkze | |
| 2007/0282358 A1 | | 12/2007 | Remiszewski et al. | |
| 2014/0107665 A1 | | 4/2014 | Shellenberger et al. | |
| 2014/0128849 A1 | | 5/2014 | Au et al. | |
| 2014/0309625 A1 | | 10/2014 | Okamoto et al. | |
| 2015/0066050 A1 | | 3/2015 | Jardine et al. | |
| 2015/0088158 A1 | | 3/2015 | Shellenberger et al. | |
| 2015/0088159 A1 | | 3/2015 | Shellenberger et al. | |
| 2017/0165019 A1 | | 6/2017 | Penny et al. | |
| 2018/0049831 A1 | | 2/2018 | Iida et al. | |
| 2018/0065243 A1 | | 3/2018 | Kim et al. | |

FOREIGN PATENT DOCUMENTS

| | | |
|---|---|---|
| JP | 2009-537280 A | 10/2009 |
| WO | WO 2007/136829 A1 | 11/2007 |
| WO | 2013/108776 A1 | 7/2013 |
| WO | 2013/116869 A1 | 8/2013 |

OTHER PUBLICATIONS

Extended Supplementary European Search Report dated Oct. 30, 2017 in European Patent Application No. 15 75 2658.3.

Office Action dated May 18, 2018 received in U.S. Appl. No. 15/235,179.

Notice of Allowance dated Sep. 21, 2018 received in U.S. Appl. No. 15/235,179.

* cited by examiner

WIRE DRIVING DEVICE AND MANIPULATOR

CROSS-REFERENCE TO RELATED APPLICATIONS

This application is a Divisional application of U.S. application Ser. No. 15/235,179 filed on Aug. 12, 2016, which is a continuation of International Application PCT/JP2015/054958, with an international filing date of Feb. 23, 2015, each of which are hereby incorporated by reference herein in its entirety. This application claims the benefit of Japanese Patent Application No. 2014-032969, the content of which is incorporated herein by reference.

TECHNICAL FIELD

The present invention relates to a wire driving device and a manipulator.

BACKGROUND ART

In the related art, there is a known manipulator having a wire driving device in which a driving source and a output shaft are connected with a wire, and the output shaft are driven by means of tensile force the driving source applies to the wire (for example, see Patent Literature 1).

This wire driving device is provided with an input pulley connected to a motor, an output pulley attached to a movable member, a tension pulley, and a wire that bridges these pulleys and that antagonistically drives the output pulley.

The tension pulley generates tension in the wire on the input-pulley side by means of a spring, thus eliminating slack in the wire.

CITATION LIST

Patent Literature

{PTL 1} Publication of Japanese Patent No. 4145464

SUMMARY OF INVENTION

Technical Problem

The present invention provides a wire driving device and a manipulator with which it is possible to compensate for slack without causing slippage of a wire on a pulley.

Solution to Problem

The present invention provides the following solutions.

An aspect of the present invention is a wire driving device including a pair of wires one ends of which are attached to a movable member and that antagonistically drive the movable member; a pair of pulleys to which the other ends of the individual wires are secured and around which the individual wires are wound; a pair of driven gears that are coaxially secured to the individual pulleys; a drive gear that is connected to a driving source that generates motive power; and a pair of movable gears that are disposed between the drive gear and the individual driven gears and that can transmit the motive power of the driving source to the driven gears from the drive gear, wherein the individual movable gears are provided in a movable manner so that the movable gears can engage with the drive gear and the driven gears when the drive gear is rotated in the direction in which the pulleys take up the wires, and so that the engagements of the movable gears with at least one of the drive gear and the driven gears can be released when the drive gear is rotated in the direction in which the pulleys let out the wires.

Another aspect of the present invention provides a manipulator including any one of the above-described wire driving devices and a joint that supports the movable member in a movable manner.

DESCRIPTION OF EMBODIMENT

A wire driving device 1 and a manipulator 2 according to an embodiment of the present invention will be described below with reference to the drawings.

Figure 1:
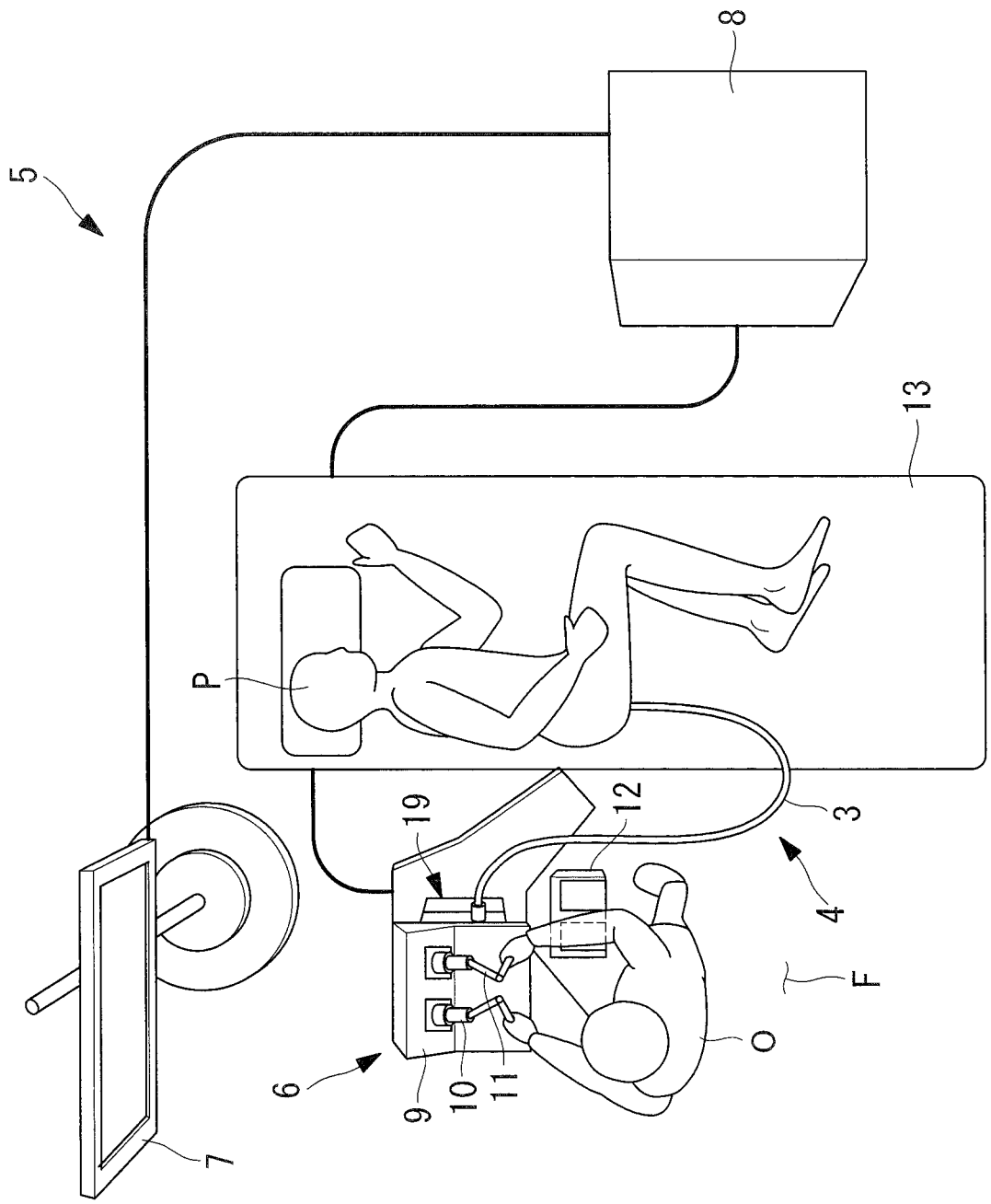
FIG. 1 is an overall configuration diagram showing a treatment manipulator system that employs a manipulator according to an embodiment of the present invention.

The manipulator 2 according to this embodiment is, for example, a treatment tool that is introduced into a body via a forceps channel (not shown) or the like provided in an inserted portion 4 of an endoscope 3 and that is used to treat an affected site, and is used in a treatment manipulator system 5 shown in FIG. 1.

As shown in FIG. 1, the treatment manipulator system 5 is provided with the endoscope 3 having the inserted portion 4 that is inserted into the body; a manipulation portion 6 that an operator O, such as a surgeon or the like, manipulates and that outputs manipulation instructions; a display portion 7 for displaying an image acquired by using the endoscope 3; and a control portion 8 that controls the endoscope 3 and the manipulator 2 in accordance with the manipulation instructions.

As shown in FIG. 1, the manipulation portion 6 includes a pair of manipulation arms 10 and 11 attached to a manipulation table 9 and a foot switch 12 placed on the floor F. The manipulation arms 10 and 11 have a multi-joint structure. The manipulation arm 10 is for performing bending manipulation of a bending portion of the inserted portion 4 of the endoscope 3, and the manipulation arm 11 is for performing bending manipulation of the manipulator 2.

A helper (not shown) makes a patient P lay down on an operating table 13 that is arranged at the manipulation portion 6, and performs appropriate treatment, such as sterilization, anesthesia, or the like.

The operator O gives instructions to the helper, prompting him/her to introduce the inserted portion 4 into the large intestine of the patient P via his/her anus. The operator O manipulates the manipulation arm 10 so as to appropriately bend the bending portion at the distal end of the inserted portion 4, thus orienting a distal-end surface, from which the distal end of the manipulator 2 protrudes, so as to face the affected site.

Figure 2:
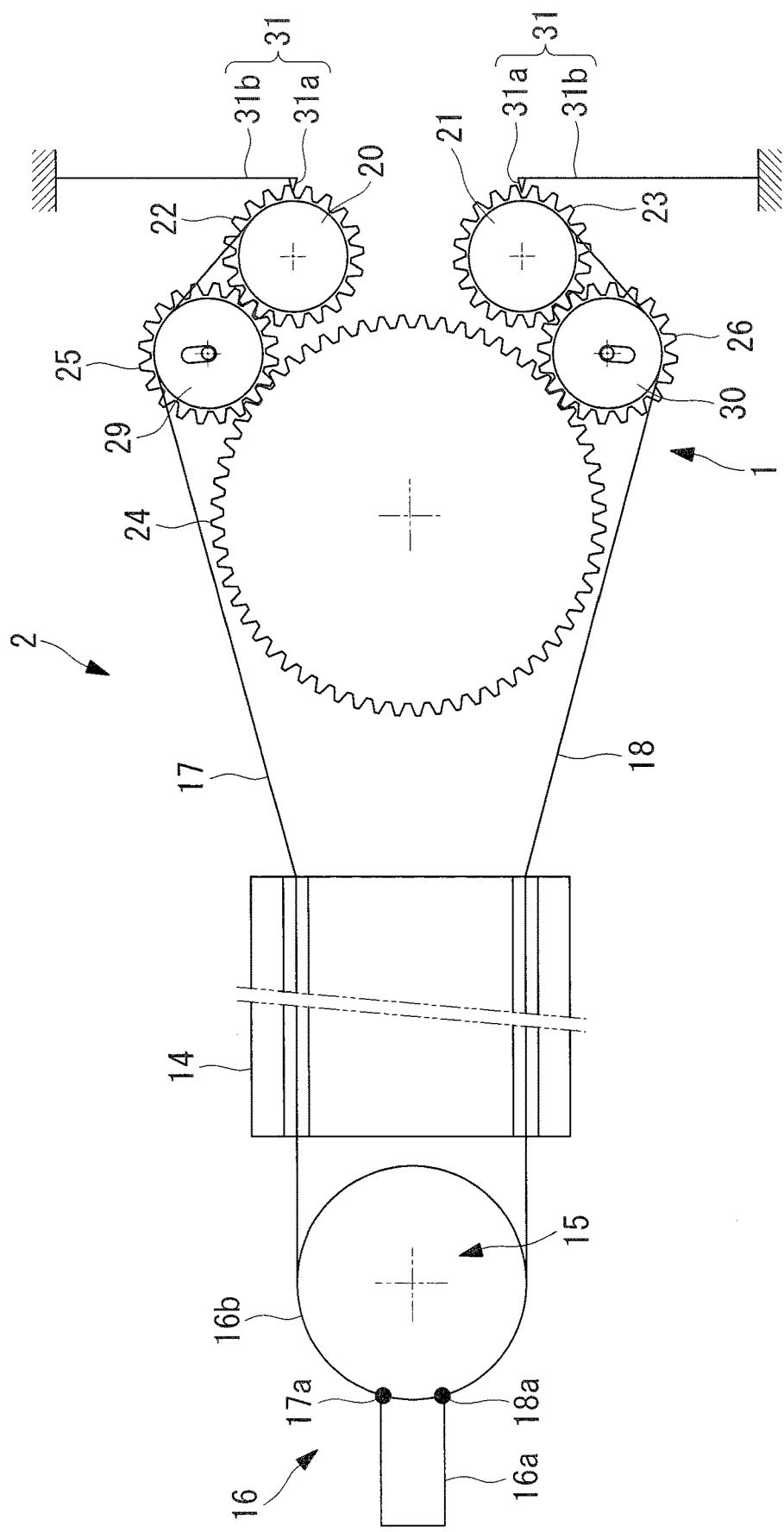
FIG. 2 is a schematic view showing the manipulator according to the embodiment of the present invention.

As shown in FIG. 2, at the distal end of a long, thin flexible portion 14 that is disposed in a state in which the flexible portion 14 is inserted into the forceps channel of the inserted portion 4 and that is bent in conformity with bending of the inserted portion 4, the manipulator 2 according to this embodiment is provided with an end effector 16 that has at least one joint 15. In addition, the manipulator 2 is provided with the wire driving device 1 that drives wires 17 and 18 that move the joint 15 toward the basal end of the flexible portion 14 and a driving portion 19 that supplies the wire driving device 1 with motive power on the basis of the instruction signals from the control portion 8.

The joint 15 of the end effector 16 pivots a distal-end portion (movable member) 16a about an axis orthogonal to the longitudinal axis of the flexible portion 14, and a distal-end pulley 16b that is supported so as to be rotatable about an axis relative to the flexible portion 14 is secured to the distal-end portion 16a. Although only one joint 15 is illustrated in the figure, more than one joint 15 may be provided.

The wire driving device 1 according to this embodiment is provided with: the pair of wires 17 and 18 in which one ends thereof are secured to the distal-end pulley 16b; a pair of take-up pulleys 20 and 21 to which the other ends of the individual wires 17 and 18 are attached and around which the individual wires 17 and 18 are wound; a pair of driven gears 22 and 23 that are coaxially secured to the take-up pulleys 20 and 21, respectively; a single drive gear 24 that is connected to the driving portion 19 and that is rotationally driven in both directions; and a pair of movable gears 25 and 26 that are individually disposed between the drive gear 24 and the individual driven gears 22 and 23.

The driving portion 19 is provided with, for example, a motor (not shown), and is configured so as to input the motive power thereof to the drive gear 24 by using a method in which the driving portion 19 has a direct connection with the drive gear 24 or the connection therebetween is made via a transmitting mechanism, such as a pulley belt, or the like.

The wires 17 and 18 are secured to the distal-end pulley 16b at the distal-end portions thereof, the wires 17 and 18 are wound around the distal-end pulley 16b in the opposite direction from individual securing points 17a and 18a, pulling forces are applied to the individual wires 17 and 18, and thus, the individual wires 17 and 18 are configured so as to individually antagonistically drive the distal-end pulley 16b clockwise or counter clockwise.

Figure 5:
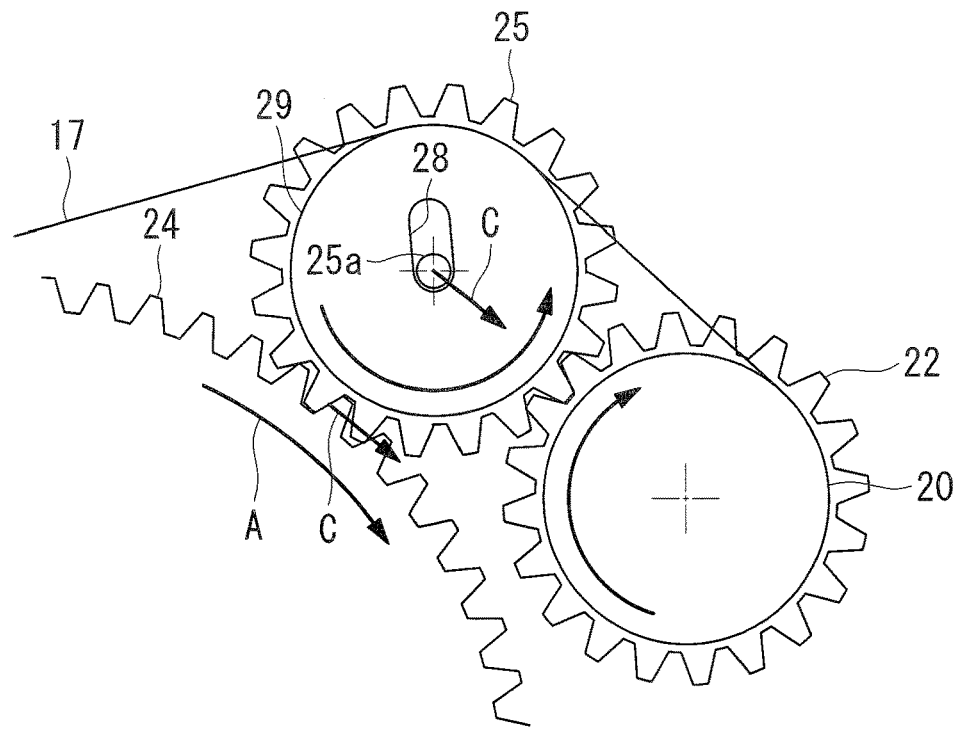
FIG. 5 is a partial magnified view showing a state in which a wire is being taken up in a wire driving device of the manipulator in FIG. 2.
Figure 6:
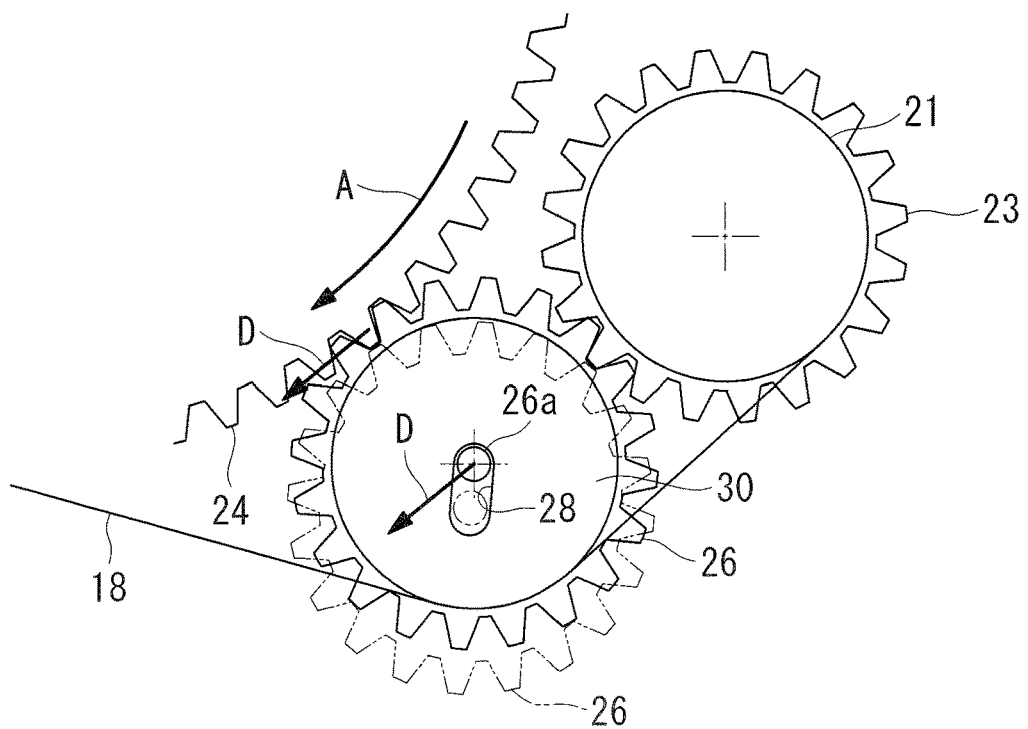
FIG. 6 is a partial magnified view showing a state in which the wire is being let out in the wire driving device of the manipulator in FIG. 2.
Figure 7:
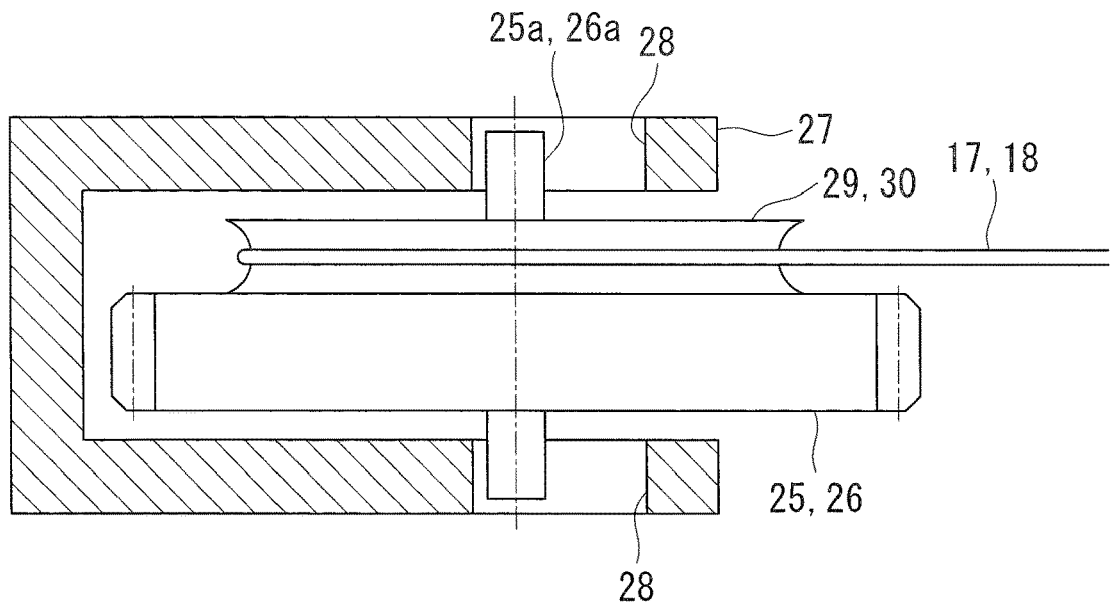
FIG. 7 is a magnified longitudinal cross-sectional view showing a movable gear and an intermediate pulley provided in the wire driving device of the manipulator in FIG. 2.

The movable gears 25 and 26 are supported so as to be movable between positions at which the movable gears 25 and 26 engage with both the drive gear 24 and the driven gear 22 (23), as shown in FIG. 5, and positions at which the engagements with the drive gear 24 and the driven gear 23 (22) are released, as shown by the broken line in FIG. 6. Specifically, as shown in FIG. 7, the movable gears 25 and 26 are supported by brackets 27 in a rotatable manner, and the brackets 27 are provided with elongated holes 28 through which shafts 25a and 26a of the movable gears 25 and 26 pass.

By doing so, the movable gears 25 and 26 can be moved in directions that intersect the shafts 25a and 26a within ranges in which the shafts 25a and 26a can be moved in the elongated holes 28. It suffices that the amounts of movement of the shafts 25a and 26a due to the elongated holes 28 be such that the engagements of the movable gears 25 and 26 with at least one of the drive gear 24 and the driven gears 22 and 23 can be released (free-wheeled).

With respect to a straight line that connects the center of the movable gear 25 (26) and the center of the drive gear 24 in the state in which the movable gear 25 (26) is engaged with both the drive gear 24 and the driven gear 22 (23), the elongated holes 28 in the bracket 27 extend, for example, in a direction that intersects with that straight line and in a direction away from the driven gear 22 (23). By doing so, the movable gear 25 (26) is configured so as to engage with both the drive gear 24 and the driven gear 22 (23) when the shaft 25 (26a) thereof is disposed at one end of each elongated hole 28, and so as to be moved to a position away from both the drive gear 24 and the driven gear 22 (23) when the shaft 25 (26a) thereof is disposed at the other end of each elongated hole 28.

In addition, intermediate pulleys 29 and 30 over which the wires 17 and 18 pass between the distal-end pulley 16b and the take-up pulleys 20 and 21 are coaxially attached to the shafts 25a and 26b of the movable gears 25 and 26 so as to be rotatable independently of the movable gears 25 and 26. The wires 17 and 18 pass over side surfaces of the intermediate pulleys 29 and 30 opposite from the drive gear 24 so as to hold down the movable gears 25 and 26 in the direction in which the movable gears 25 and 26 engage with the drive gear 24 when tensile forces are applied to the wires.

In addition, braking means 31 for maintaining the driven gears 22 and 23 in a stationary state are provided in the wire driving device 1 according to this embodiment. The braking means 31 are provided with, for example, in the example shown in FIG. 2, engaging portions 31a that are disposed in tooth spaces of the driven gears 22 and 23 and plate springs 31b that bias the engaging portions 31a into the tooth spaces. By doing so, when the movable gears 25 and 26 engage with the drive gear 24 and the driven gears 22 and 23, and the driven gears 22 and 23 are rotationally driven, the plate springs 31b deform, and the engaging portions 31a are released from the tooth spaces, thus allowing the driven gears 22 and 23 to be rotated. On the other hand, when the engagements of the movable gears 25 and 26 with the drive gear 24 and the driven gears 22 and 23 are released, the engaging portions 31a are positioned in the tooth spaces, and the driven gears 22 and 23 are maintained at those positions in stationary states, unless tensile forces equal to or greater than a predetermined level act on the wires 17 and 18. In other words, in the case in which the torques applied to the take-up pulleys 20 and 21 are equal to or less than a predetermined value, the take-up pulleys 20 and 21 are maintained in stationary states, preventing the rotation thereof.

The operation of the thus-configured wire driving device 1 and manipulator 2 according to this embodiment will be described below.

In the treatment manipulator system 5, when manipulation instructions are input to the control portion 8 in response to manipulation of the manipulation arm 11 of the manipulation portion 6, the control portion 8 activates the driving portion 19 of the manipulator 2, and the motive power from the driving portion 19 is input to the wire driving device 1.

Figure 3:
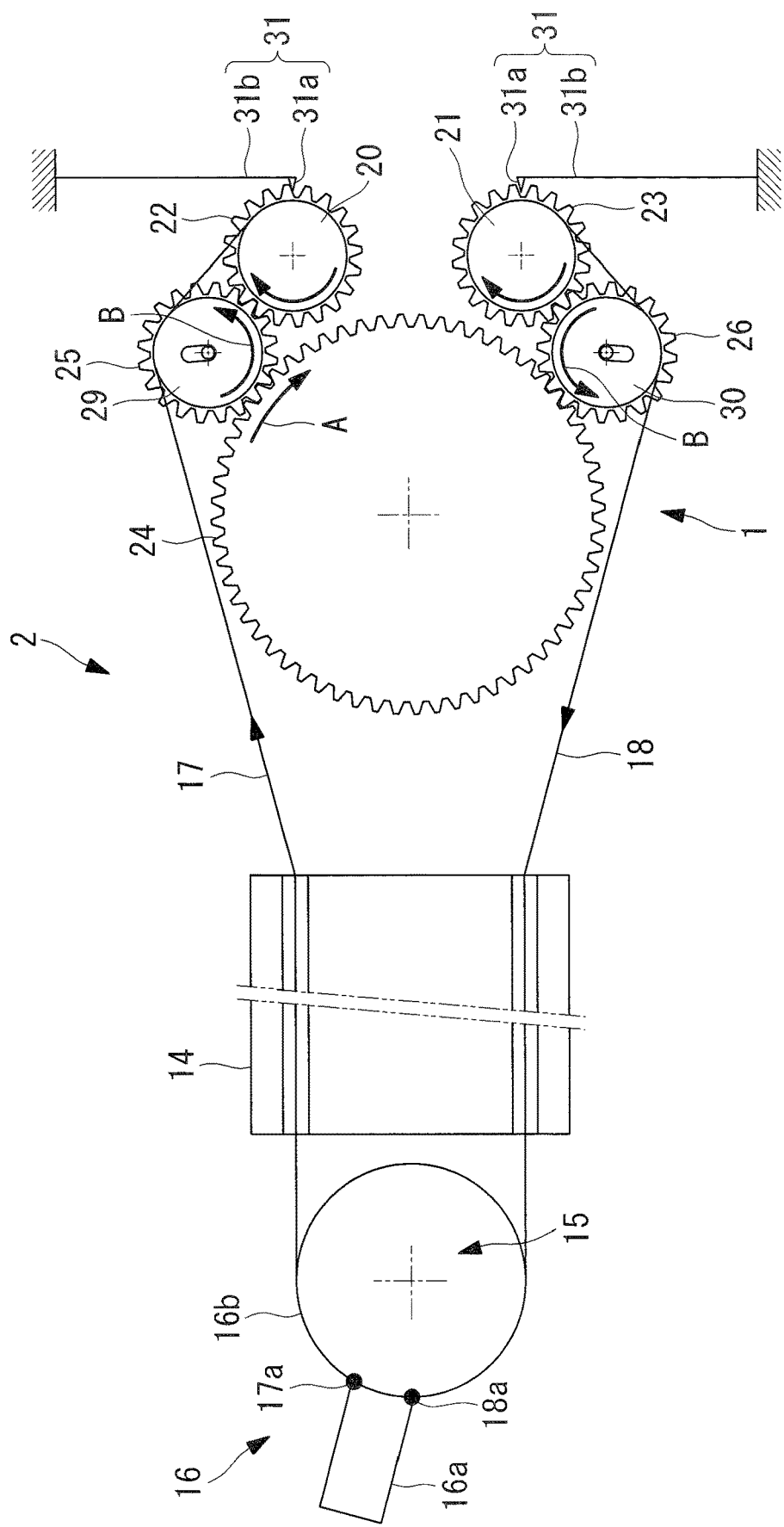
FIG. 3 is a schematic view showing a state in which an end effector of the manipulator in FIG. 2 starts to be driven in one direction.

In the case in which manipulation instructions are input so as to pivot the end effector 16 at the distal end of the manipulator 2 in one direction about the shaft of the distal-end pulley 16b, the drive gear 24 is rotated in one direction (direction of the arrow A shown in FIG. 3) due to the motive power transmitted from the driving portion 19. Because some tensile forces are applied to the wires 17 and 18 at that time, both of the movable gears 25 and 26 are moved to the positions at which the movable gears 25 and 26 engage with the drive gear 24 and the driven gears 22 and 23 due to the tensile forces generated in the wires 17 and 18, and thus, the movable gears 25 and 26 begin to individually be rotationally driven in the direction of the arrow B due to the rotation of the drive gear 24.

At this time, because the movable gear 25 receives a force from the drive gear 24 in the direction of the arrow C, as shown in FIG. 5, the movable gear 25 is biased so as to be moved in this direction, and the engagements thereof with the drive gear 24 and the driven gear 22 are reinforced. Furthermore, when the motive power received from the drive gear 24 rotates the movable gear 25, the rotational force is transmitted to the driven gear 22.

When the motive power that rotates the driven gear 22 becomes equal to or greater than the predetermined value at which the braking forces of the braking means 31 are exceeded, the stationary states maintained by the braking means 31 are canceled, thus allowing the driven gear 22 to be rotated. By doing so, the take-up pulley 20 that is coaxially secured to the driven gear 22 is rotated in the direction in which the wire 17 is taken up.

Then, because the tensile force in the wire 17 is increased when the take-up pulley 20 is rotated, thus increasing the force that biases the movable gear 25 in the direction in which the movable gear 25 is engaged with the drive gear 24 and the driven gear 22, the engagements among these gears 22, 24, and 25 are maintained. When the tensile force in the wire 17 is increased, the distal-end pulley 16b to which the distal end of the wire 17 is secured is rotated, and the distal-end portion 16a of the end effector 16 secured to the distal-end pulley 16b is pivoted in one direction.

Figure 4:
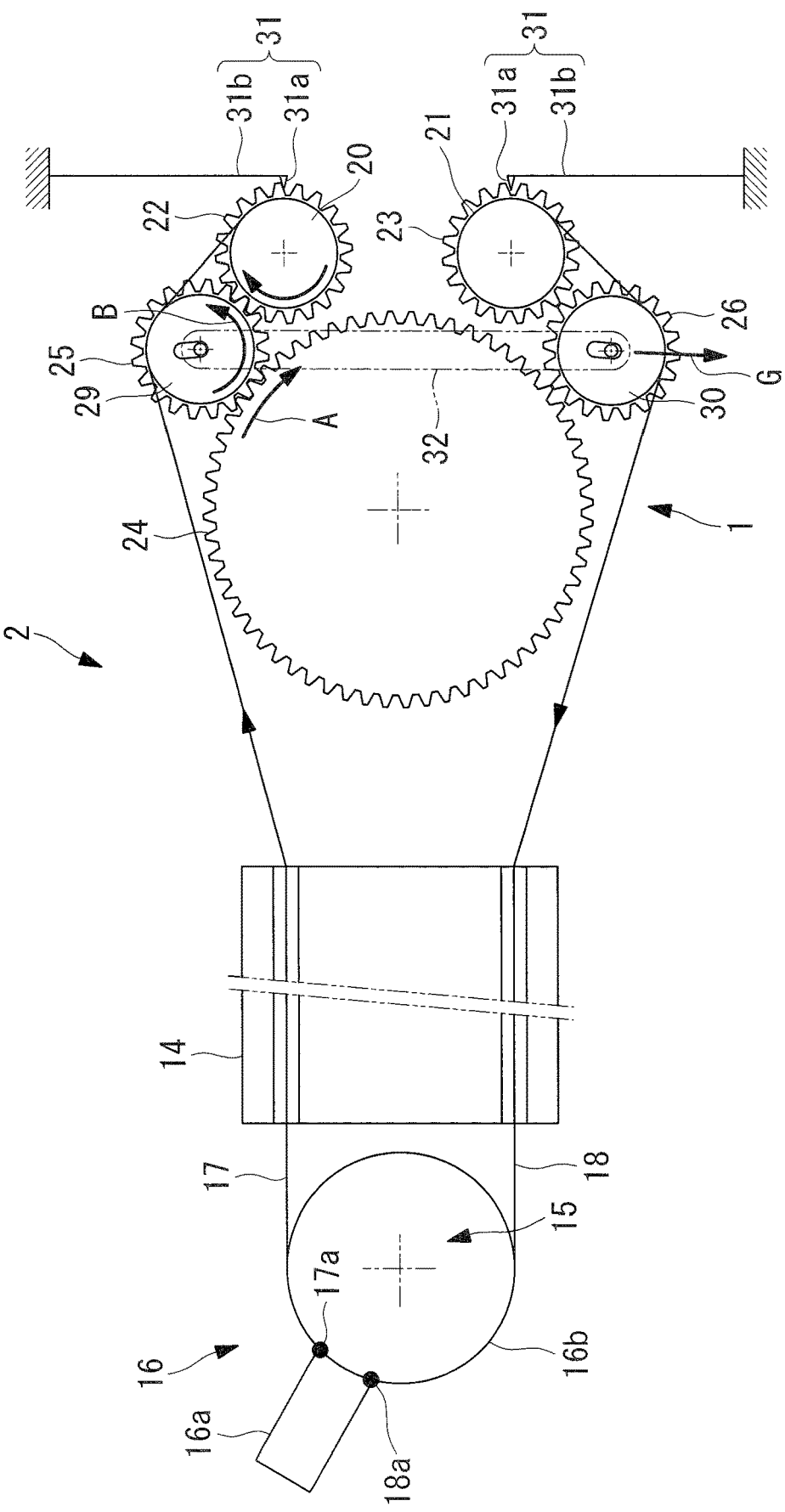
FIG. 4 is a schematic view showing a state in which the end effector of the manipulator in FIG. 2 is further driven in the same direction as in FIG. 3.

When the drive gear 24 is rotationally driven in the above-described direction A, because the other movable gear 26 receives a force from the drive gear 24 in the direction of the arrow D, as shown in FIG. 6, the movable gear 26 is biased so as to be moved in this direction, thus being moved in a direction G in which the engagements with the drive gear 24 and the driven gear 23 are released, as shown in FIG. 4.

In the state in which the drive gear 24 is engaged with the movable gear 26 and the driven gear 23, because the driven gear 23 is rotated in the direction in which the wire 18 is let out from the take-up pulley 21, the tensile force in the wire 18 is decreased, thus facilitating the movement of the movable gear 26 in the direction in which the engagements thereof with the drive gear 24 and the driven gear 23 are released, as indicated by the chain line in FIG. 6.

In this case, because the wire 17 (18) is stretched due to the tensile force in the case in which a large tensile force acts on the wire 17 (18) on the take-up side, the pivoting angle of the joint 15 of the end effector 16 is not proportional to the amount by which the wire 17 (18) is taken up, and thus, it is necessary to take up an additional amount of the wire 17 (18) beyond an amount by which the wire 17 (18) needs to be taken up to achieve pivoting by a desired angle. Therefore, the drive gear 24 rotates the driven gear 22 (23), to which the take-up pulley 20 (21) that takes up the wire 17 (18) is secured, by an additional amount.

At this time, in the state in which the driven gear 23 (22) is engaged with the drive gear 24 via the movable gear 26 (25), the driven gear 23 (22), to which the take-up pulley 21 (20) that lets out the wire 18 (17) is secured, is rotated in accordance with the rotation of the drive gear 24, thus forcing the take-up pulley 21 (20) to let out the wire 18 (17). Then, when the amount by which the wire 18 (17) needs to be let out to pivot the joint 15 of the end effector 16 by a desired pivoting angle is exceeded, the tensile force in the wire 18 (17) becomes low enough for the movable gear 26 (25) to move in the direction that intersects the shaft 26a (25a). By doing so, because the engagements of the movable gear 26 (25) with the drive gear 24 and the driven gear 23 (22) are released, thus causing free wheeling, even if the drive gear 24 is rotated by an additional amount beyond the required amount, an additional amount of the wire 18 (17) is not let out from the take-up pulley 21 (20), and thus, it is possible to prevent slack in the wire 18 (17).

In this case, with the wire driving device 1 and the manipulator 2 according to this embodiment, unlike the wire driving devices in the related art, because slack in the wires 17 and 18 is prevented not by causing slipping between the pulley and the wires but by releasing the engagements of the movable gear 25 (26) with the drive gear 24 and driven gear 22 (23), there is an advantage in that it is possible to more reliably prevent slack.

In addition, in the case where the direction in which the drive gear 24 is rotated is reversed, because the movable gear 26 (25) is moved in the direction in which the movable gear 26 (25) engages with the drive gear 24 and the driven gear 23 (22), which has previously served to let out the wire, the motive force is transmitted to the driven gear 23 (22) from the drive gear 24 via the movable gear 26 (25), the driven gear 23 (22) rotates the take-up pulley 21 (20) in the take-up direction, thus taking up the wire 18 (17), and thus, the joint 15 of the manipulator 2 is pivoted in the opposite direction. In this case, because the wire 18 (17) is prevented from becoming slack during the pivoting operation before the reversal of the rotation direction, take-up of the wire 18 (17) is quickly initiated after the reversal of the rotation direction of the drive gear 24. In other words, there is an advantage in that the joint 15 can be pivoted in the opposite direction without causing a delay due to hysteresis.

Note that, in this embodiment, although the elongated holes 28 provided in the brackets 27 that support the movable gears 25 and 26 extend in the direction in which the engagements of the movable gear 25 (26) with both the drive gear 24 and the driven gear 22 (23) are released, there is no limitation thereto. For example, the elongated holes 28 may be provided so as to be movable in a direction in which only the engagement with the drive gear 24 is released or a direction in which only the engagements with the driven gears 22 and 23 are released.

Figure 8:
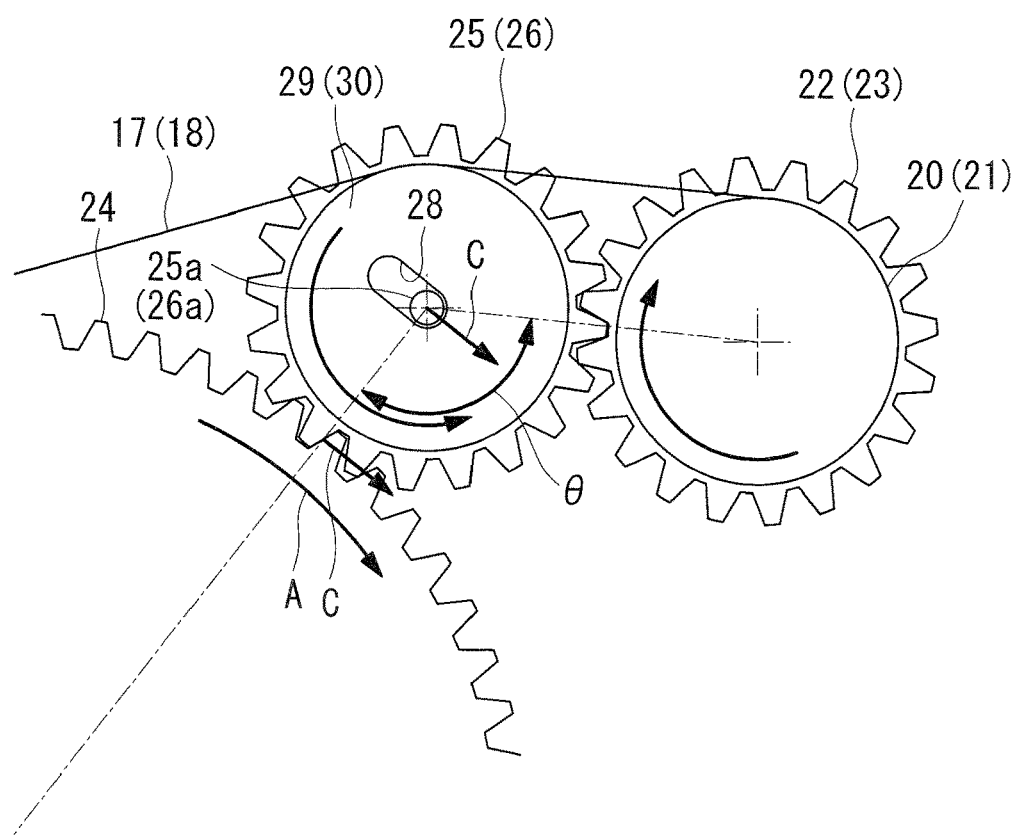
FIG. 8 is a partial magnified view showing a state in which the wire is being taken up in a first modification of the wire driving device of the manipulator in FIG. 2.
Figure 9:
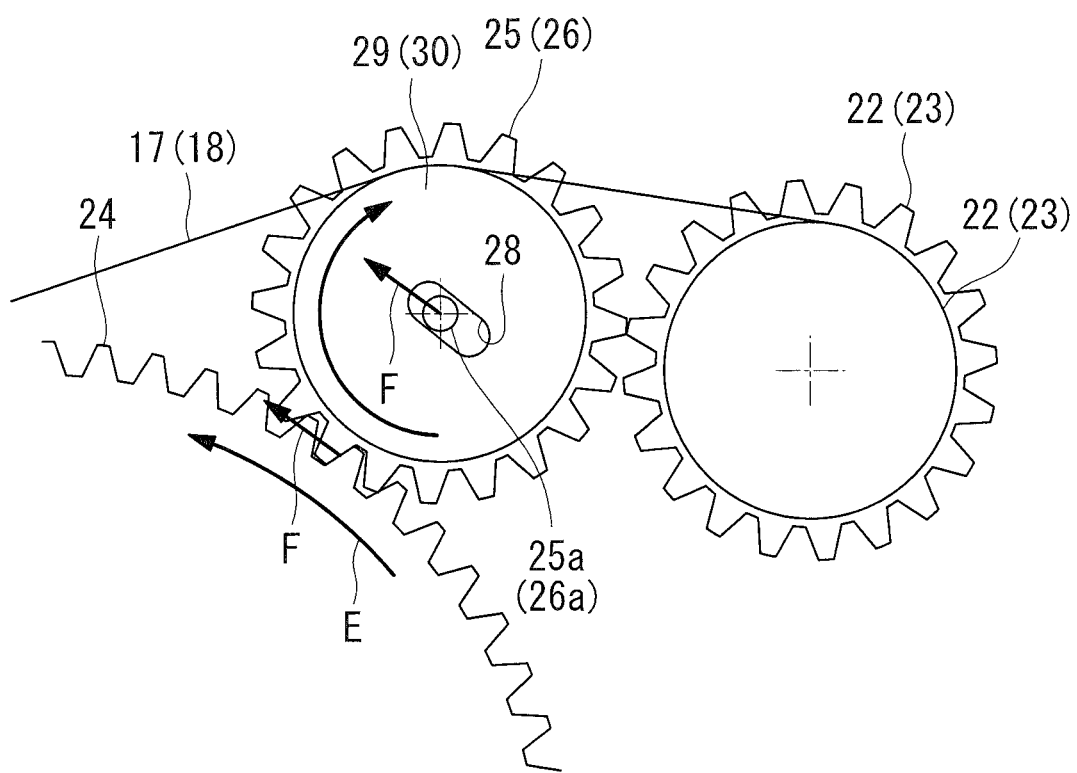
FIG. 9 is a partial magnified view showing a state in which the wire is being let out in the first modification of the wire driving device of the manipulator in FIG. 2.

In particular, it is preferable that the elongated holes 28 be provided so as to extend in the direction parallel to the tangent lines of the drive gear 24 or so as to take an arc shape in which the center thereof is at the center of the drive gear 24, as shown in FIGS. 8 and 9. In this case, the engagements of the drive gear 24 with the movable gears 25 and 26 are always maintained, and the movable gears 25 and 26 and the driven gears 22 and 23 engage and disengage depending on the positions of the movable gears 25 and 26.

As shown in FIG. 8, when the drive gear 24 is driven in the direction A in which the wire 17 (18) is taken up, the movable gear 25 (26) is moved along the elongated hole 28 in the direction toward the driven gear 22 (23) due to the force received from the drive gear 24 in the direction of the arrow C. By doing so, the movable gear 25 (26) engages with the driven gear 22 (23), the motive power is transmitted to the driven gear 22 (23) from the drive gear 24, and thus, the wire 17 (18) is taken up. Note that, although the direction of the arrow C is, to be accurate, a direction in which the pressure angle of the gear is added to the tangential direction, it is described as a substantially tangential direction here, and it will be described in the same manner hereinafter also.

On the other hand, when the drive gear 24 is driven in a direction E in which the wire 17 (18) is let out, as shown in FIG. 9, the driven gear 22 (23) is rotated by the motive power from the drive gear 24, thus initially forcing the wire 17 (18) to be let out. Then, when the tensile force in the wire 17 (18) decreases, the movable gear 25 (26) is moved along the elongated hole 28 in the direction away from the driven gear 22 (23) due to the force received from the drive gear 24 in the direction of the arrow F. By doing so, the engagement of the movable gear 25 (26) with the driven gear 22 (23) is released, and thus, the wire 17 (18) stops being forcedly let out by the drive gear 24.

In other words, because an additional amount of the wire 18 (17) is prevented from being let out from the take-up pulley 23 (22) on the let-out side, even if the additional amount of the wire 17 (18) is taken up by the take-up pulley 22 (23) on the take-up side, it is possible to prevent the wire 18 (17) on the let-out side from becoming slack. Because the engagements of the movable gears 25 and 26 and the drive gear 24 are always maintained, and the engagement is released only between the movable gear 25 (26) and the driven gear 22 (23), there is an advantage in that it is possible to more reliably switch between taking up of the wire 17 (18) and letting out of the wire 17 (18) without causing slacking thereof.

In this case, it is desirable that an angle θ formed by a straight line connecting the center of the drive gear 24 and that of the movable gear 25 (26) and a straight line connecting the center of the movable gear 25 (26) and that of the driven gear 22 (23) be equal to or greater than 90° and equal to or less than 135°. When the angle θ is less than 90°, the reaction from the driven gear 22 (23) facilitates the movement of the movable gear 25 (26) along the elongated hole 28 in the direction that causes free wheeling when the tensile force applied to the wire 17 (18) is increased. In addition, when the angle θ is greater than 135°, it becomes less likely for the engagement of the movable gear 25 (26) with the driven gear 22 (23) to be released when letting out the wire 17 (18).

In addition, in order to more reliably engage the movable gear 25 (26) with the driven gear 22 (23) when taking up the wire 17 (18), it is permissible to provide a movable-gear biasing means (not shown), such as a spring or the like, that biases the movable gear 25 (26) in the direction in which the movable gear 25 (26) is moved along the elongated hole 28 toward the driven gear 22 (23).

In addition, as indicated by the chain line in FIG. 4, the shafts 25a and 26a of the movable gears 25 and 26 may be coupled with each other by using a linkage 32. By doing so, when the movable gear 25 (26) is placed at the position at which the movable gear 25 (26) engages with the drive gear 24 and the driven gear 22 (23), it is possible to always place the other movable gear 26 (25) at the position at which the engagements with the drive gear 24 and the driven gear 23 (22) are released.

Figure 10:
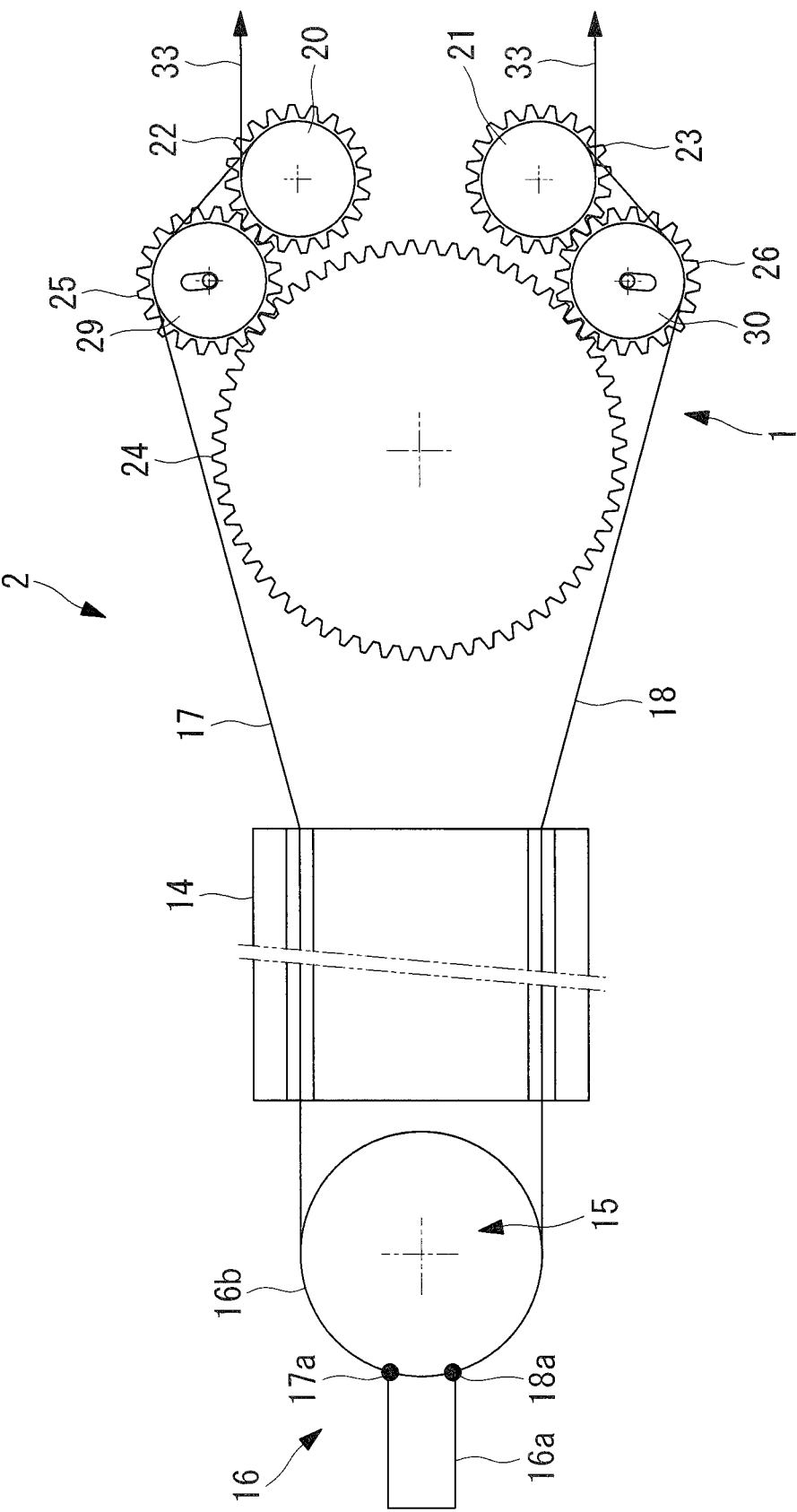
FIG. 10 is a schematic view showing a second modification of the wire driving device of the manipulator in FIG. 2.

In addition, although an example having the engaging portion 31a and the plate spring 31b has been described as the braking means 31, alternatively, it is permissible to employ biasing means such as springs 33 that always bias the driven gears 22 and 23 in the direction in which the wires 17 and 18 are taken up, as shown in FIG. 10.

Figure 11:
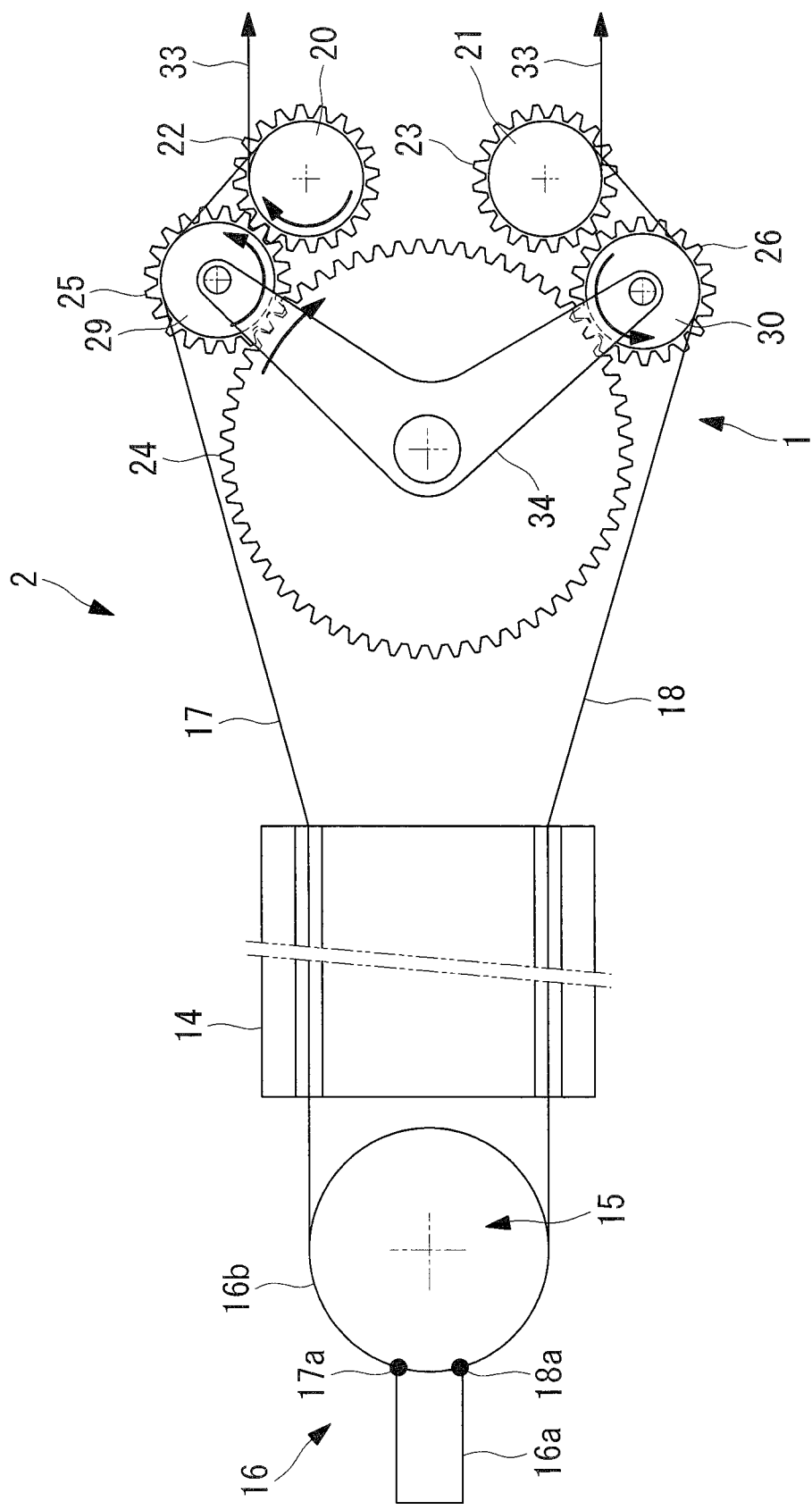
FIG. 11 is a schematic view showing a third modification of the wire driving device of the manipulator in FIG. 2.

In addition, in FIGS. 8 and 9, the movable gears 25 and 26 are supported in a movable manner by the elongated holes 28 that extend in the direction parallel to the tangent lines of the drive gear 24 or that take an arc shape in which the center thereof is at the center of the drive gear 24; alternatively, however, the two movable gears 25 and 26 may be coupled by using a linkage 34 that is attached so as to be pivotable about the center shaft of the drive gear 24, as shown in FIG. 11. By doing so, when the movable gear 25 (26) is engaged with the driven gear 22 (23), it is possible to release the engagement of the other movable gear 26 (25) with the driven gear 23 (22), and thus, there is an advantage in that it is possible to more reliably switch between taking up of the wire 17 (18) and letting out of the wire 17 (18) without causing slacking thereof.

Figure 12:
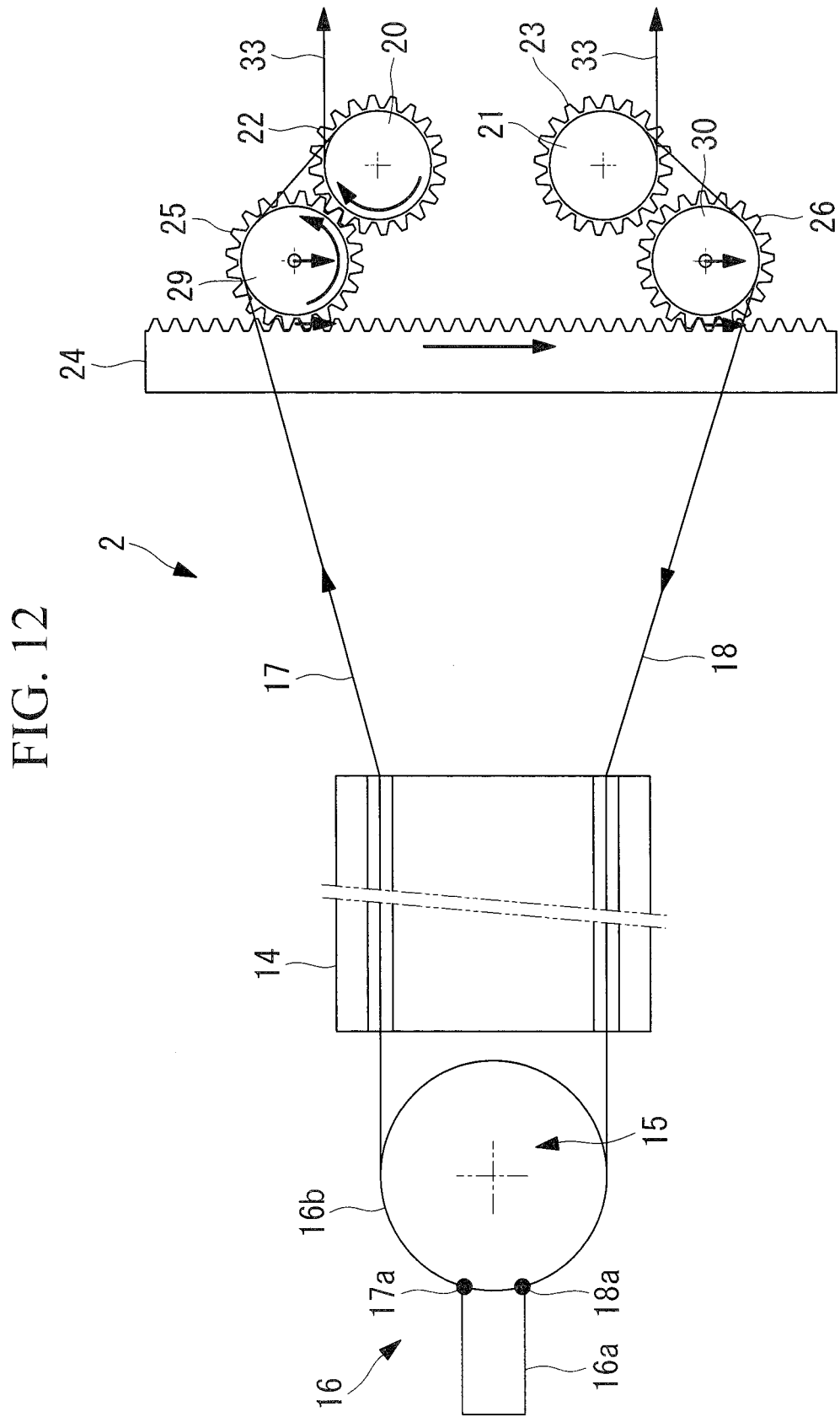
FIG. 12 is a schematic view showing a fourth modification of the wire driving device of the manipulator in FIG. 2.

In addition, in this embodiment, although a discoid gear has been described as an example of the drive gear 24, alternatively, the drive gear 24 may be formed of a rack gear that can be moved in the longitudinal direction in a reciprocating manner, as shown in FIG. 12. In this case, the movable gears 25 and 26 having a tooth profile that allows engagement with the drive gear 24 and the driven gears 22 and 23 may be employed and provided so as to be movable in the longitudinal direction of the rack gear. By doing so, it is possible to switch the states of the engagement between the movable gears 25 and 26 and the driven gears 22 and 23 while the movable gears 25 and 26 are maintained in the state in which the movable gears 25 and 26 are always engaged with the drive gear 24.

Figure 13:
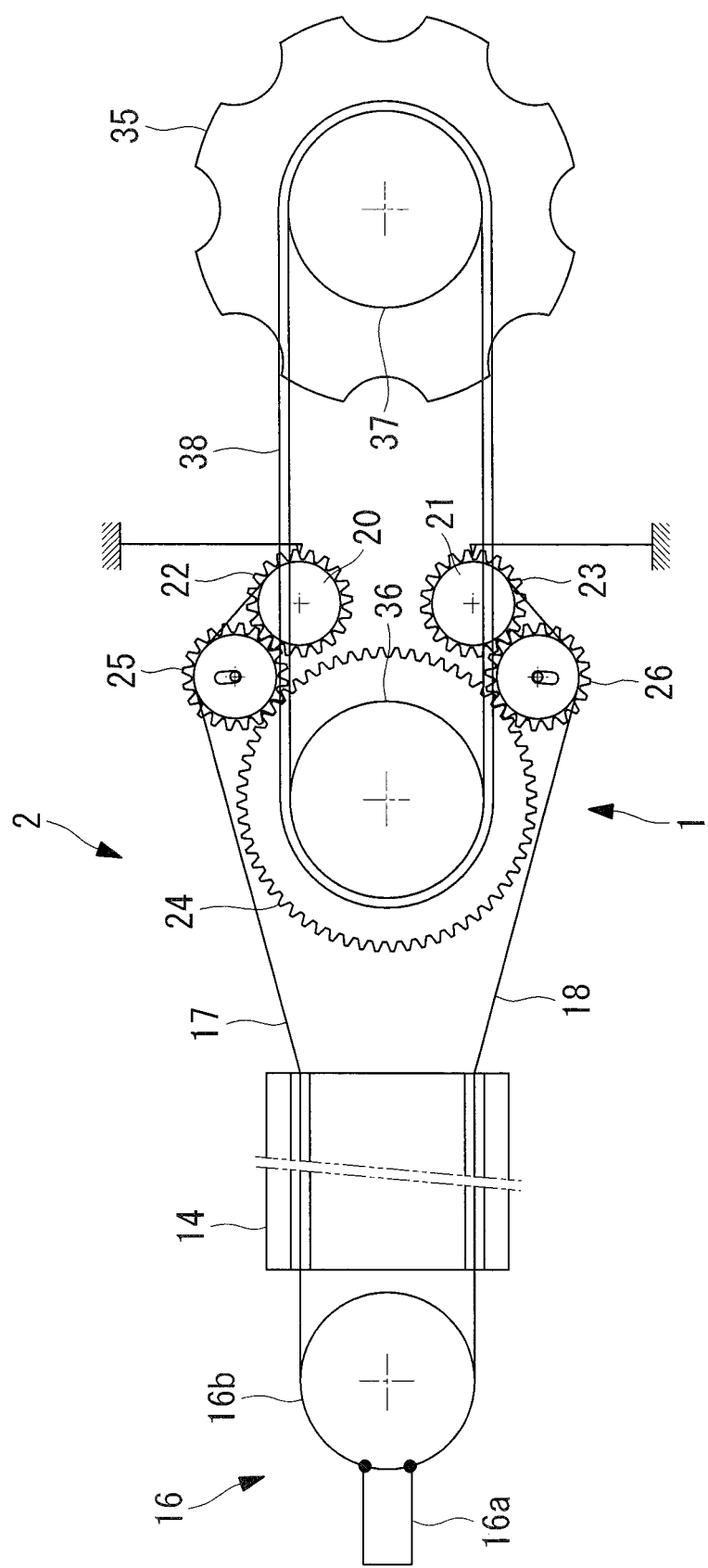
FIG. 13 is a schematic view showing a fifth modification of the wire driving device of the manipulator in FIG. 2.

In addition, in this embodiment, although the electric manipulator 2 in which the driving portion 19 has the motor that supplies the motive power to the drive gear 24 has been described as an example, alternatively, as shown in FIG. 13, a manual manipulator provided with, as a driving source, a manually manipulated handle 35, pulleys 36 and 37 provided at the drive gear 24 and the handle 35, and a belt 38 that passes over these pulleys 36 and 37 may be employed.

Figure 14:
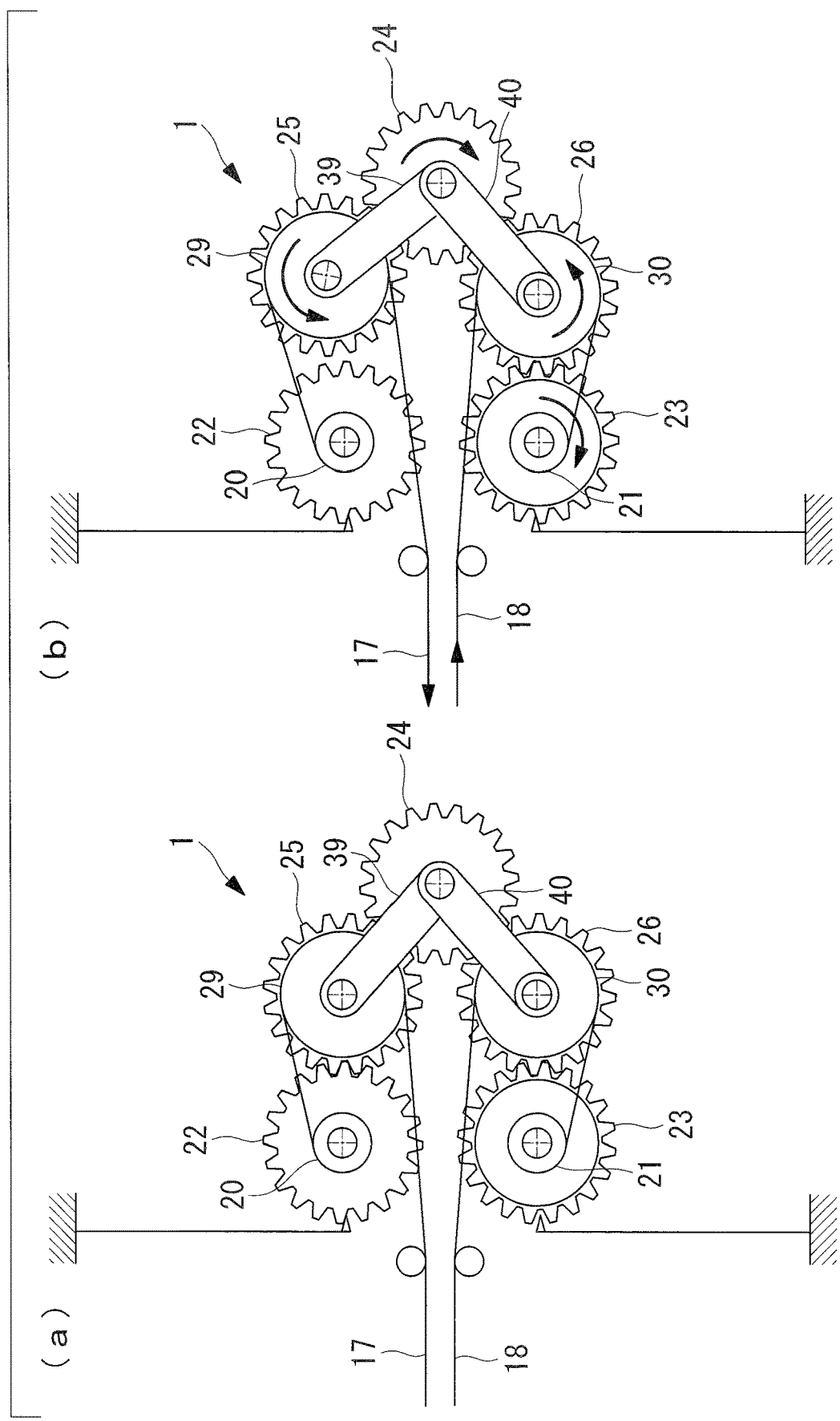
FIG. 14 is (a) a schematic view showing the configuration of a sixth modification of the wire driving device of the manipulator in FIG. 2, and (b) a schematic view showing the operation of gears when a drive gear is rotated in one direction.

In addition, in this embodiment, the wires 17 and 18 may be threaded, as shown in FIG. 14(a). In other words, in this wire driving device 1, the shaft of the drive gear 24 and those of the movable gears 25 and 26 are connected by using separate linkages 39 and 40 that are independent of each other so as to be pivotable about the shaft of the drive gear 24, and the wires threaded on the opposite sides of the take-up pulleys 20 and 21 over substantially 180°, flanking the shafts of the intermediate pulleys 29 and 30 that are coaxial with the movable gears 25 and 26, are guided toward the distal-end pulley 16b.

When the drive gear 24 is rotated clockwise in the state in which the movable gear 25 is engaged with the driven gear 22, as shown in FIG. 14(a), because the take-up pulley 20 is rotated clockwise and the wire 17 is let out, as shown in FIG. 14(b), the tensile force in the wire 17 rapidly decreases.

When the force that holds down the movable gear 25 and the driven gear 22, generated by the tensile force in the wire 17, drops below the force that acts in the direction in which the drive gear 24 moves the movable gear 25 away from the driven gear 22 due to a decrease in the tensile force in the wire 17, because the movable gear 25 supported by the linkage 39 is pivoted clockwise centered on the shaft of the drive gear 24 and the engagement with the driven gear 22 is released, any further letting-out of the wire 17 is stopped.

In addition, when the drive gear 24 is rotated clockwise in the state in which the movable gear 26 is engaged with the driven gear 23, because the take-up pulley 21 is rotated clockwise and the wire 18 is taken up, the tensile force in the wire 18 increases. Furthermore, because the movable gear 26 supported by the linkage 40 receives a force from the drive gear 24 in the direction toward the driven gear 23, the movable gear 26 is pivoted clockwise centered on the shaft of the drive gear 24, and the engagement thereof with the driven gear 23 is reinforced.

In particular, with such a wire driving device 1, because the wire 18 is folded back via the intermediate pulley 30, the tensile force that acts on the intermediate pulley 30 is doubled, and it is possible to make free wheeling between the movable gear 26 and the driven gear 23 less likely to occur during take-up.

Although the operation is reversed from that described above when the drive gear 24 is put in reverse, after the reversal, because it is necessary to quickly separate the movable gear 25 (26) and the driven gear 22 (23) in the engaged state and to engage the movable gear 26 (25) and the driven gear 23 (22) in the separated state, a biasing means, such as a torsion spring (not shown), for biasing in the direction in which the linkages 39 and 40 spread out may be provided.

Note that a physical stopper (not shown) may be provided so that the movable gears 25 and 26 supported by the linkages 39 and 40 are not excessively held down against the driven gears 22 and 23 by the tensile forces in the wires 17 and 18, that is, so that the shaft-to-shaft distances between the shafts of the movable gears 25 and 26 and the shafts of the driven gears 22 and 23 do not become more compressed as compared with the sum of the respective pitch circle radii.

As a result, the above-described embodiment leads to the following aspects.

An aspect of the present invention is a wire driving device including a pair of wires one ends of which are attached to a movable member and that antagonistically drive the movable member; a pair of pulleys to which the other ends of the individual wires are secured and around which the individual wires are wound; a pair of driven gears that are coaxially secured to the individual pulleys; a drive gear that is connected to a driving source that generates motive power; and a pair of movable gears that are disposed between the drive gear and the individual driven gears and that can transmit the motive power of the driving source to the driven gears from the drive gear, wherein the individual movable gears are provided in a movable manner so that the movable gears can engage with the drive gear and the driven gears when the drive gear is rotated in the direction in which the pulleys take up the wires, and so that the engagements of the movable gears with at least one of the drive gear and the driven gears can be released when the drive gear is rotated in the direction in which the pulleys let out the wires.

With the wire driving device according to this aspect, when the driving source is driven in one direction, the drive gear attached to the driving source is actuated in one direction. At this time, because the drive gear is rotated in the direction in which one of the wires secured to the one of the pulleys is taken up by the pulley, one of the movable gears is moved in the direction in which this movable gear engages with one of the driven gears, which is secured to the one pulley that takes up the one wire, and the drive gear. By doing so, the motive power of the driving source is transmitted to one of the pulleys via the drive gear, the movable gear, and the driven gear, the tensile force in the wires increase when the wires are taken up by the pulley, and thus, the movable member to which one ends of the wires are attached is moved in one direction.

On the other hand, with respect to the other wire secured to the other pulley, because the drive gear is rotated in the direction in which the wire is let out from the pulley, the other movable gear is moved in the direction in which the engagement thereof with at least one of the other driven gear and the drive gear is released. Therefore, the other wire is not forcedly let out via the engagements of the drive gear and the movable gear and the driven gear, and the other wire is passively let out in accordance with the tensile force thereof.

In other words, even if one of the wires stretches by being pulled and the drive gear is driven so that one of the pulleys takes up the wire in a greater amount than the amount by which the movable member is moved, it is possible to prevent slacking because the other wire is let out by an amount corresponding to the amount by which the movable member is moved.

As a result, because the wires are pulled and slacking is prevented not by causing the wires to slip at the pulleys as in the related art but by engaging the gears, it is possible to antagonistically drive the movable member, while more reliably compensating for slacking, without depending on unreliable adjustment of the coefficient of friction.

The above-described aspect may be provided with a braking means for maintaining the pulleys in a stationary state, preventing the rotation thereof, when torques exerted on the pulleys are equal to or less than a predetermined value.

By doing so, because the braking means maintains the pulleys in stationary states when the engagement of the drive gear with at least one of the movable gears and the driven gears is released, it is possible to prevent a problem in which the wire is let out due to unintentional rotation of the pulleys.

In addition, the above-described aspect may be provided with a take-up biasing means for biasing the individual pulleys in directions in which the wires are taken up.

By doing so, because the wire is taken up by the pulley that is biased by the take-up biasing means in the direction in which the wire is taken up when the engagement of the drive gear with at least one of the movable gears and the driven gears is released, it is possible to prevent a problem in which the wire is unintentionally let out from the pulley.

In addition, the above-described aspect may be provided with a movable-gear biasing means for biasing the movable gears in the direction in which the movable gears are engaged with the drive gear and the driven gears.

By doing so, the movable gears biased by the movable-gear biasing means are engaged with the drive gear and the driven gears, and thus, it is possible to quickly transmit the motive power to the driven gears via the movable gears, when the drive gear is rotated in the direction in which the wire is taken up, and it is possible to cut the transmission of the motive power by means of so-called "free wheeling" in which engagement is released due to the movement of the movable gears, when the drive gear is rotated in the direction in which the wire is let out.

In addition, another aspect of the present invention provides a manipulator including any one of the above-described wire driving devices and a joint that supports the movable member in a movable manner.

With this aspect, because the slacking of the wires is prevented by the wire driving device, it is possible to prevent the occurrence of a problem in which the operation of the movable member is stopped while eliminating slack when the direction in which the movable member is moved is reversed, and thus, it is possible to achieve quick operation without hysteresis.

The present invention affords an advantage in that it is possible to compensate for slack without causing slippage of a wire on a pulley.

REFERENCE SIGNS LIST 1 wire driving device
2 manipulator
15 joint
16a distal-end portion (movable member)
17, 18 wire
19 driving portion (driving source)
20, 21 take-up pulley (pulley)
22, 23 driven gear
24 drive gear
25, 26 movable gear
29, 30 intermediate pulley (movable pulley)
31 braking means
33 spring (take-up biasing means)

What is claimed is:

1. A wire driving device comprising:
a pair of wires, one end of each individual wire in the pair of wires being attached to a movable member for antagonistically driving the movable member;
a pair of pulleys, an other end of each individual wire in the pair of wires being secured to an individual pulley in the pair of pulleys, each individual wire being wound around a respective one of each individual pulley;
a pair of driven gears, each driven gear in the pair of driven gears being coaxially secured to a respective one of each individual pulley;
a drive gear that is connected to a driving source that generates motive power;
a pair of movable gears, each individual movable gear of the pair of movable gears being disposed between the drive gear and a respective one of each individual driven gear, each individual movable gear transmitting the motive power of the driving source to the respective driven gear from the drive gear; and
a movable-gear means for moving each individual movable gear in a direction in which each individual movable gear is engaged with the drive gear and a respective individual driven gear.

2. The wire driving device according to claim 1, wherein the movable-gear means is configured such that each individual movable gear is provided in a movable manner so that the pair of movable gears engage with the drive gear and with each respective individual driven gear when the drive gear is rotated in a manner in which the pair of pulleys wind a respective wire.

3. The wire driving device according to claim 1, wherein the movable-gear means is configured such that each individual movable gear is provided in a movable manner so that engagement of one individual movable gear with at least one of the drive gear and a respective individual driven gear is released when the drive gear is rotated in a manner in which a respective pulley unwinds a respective wire.

4. The wire driving device according to claim 1, further comprising a pair of movable pulleys, each individual movable pulley of the pair of movable pulleys being coaxially disposed at a respective individual movable gear,
wherein a respective individual wire passes over each individual movable pulley on opposite sides of, flanking shafts thereof, the positions at which each respective movable gear engages with at least one of the drive gear and a respective individual driven gear.

5. A manipulator comprising:
a wire driving device comprising:
a pair of wires, one end of each individual wire in the pair of wires being attached to a movable member for antagonistically driving the movable member;
a pair of pulleys, an other end of each individual wire in the pair of wires being secured to an individual pulley in the pair of pulleys, each individual wire being wound around a respective one of each individual pulley;
a pair of driven gears, each driven gear in the pair of driven gears being coaxially secured to a respective one of each individual pulley;
a drive gear that is connected to a driving source that generates motive power;
a pair of movable gears, each individual movable gear of the pair of movable gears being disposed between the drive gear and a respective one of each individual driven gear, each individual movable gear transmitting the motive power of the driving source to the respective driven gear from the drive gear;
a movable-gear means for moving each individual movable gear in a direction in which each individual movable gear is engaged with the drive gear and a respective individual driven gear; and
a joint that supports the movable member in a movable manner.

6. The manipulator according to claim 5, wherein the movable-gear means is configured such that each individual movable gear is provided in a movable manner so that the pair of movable gears engage with the drive gear and with each respective individual driven gear when the drive gear is rotated in a manner in which the pair of pulleys wind a respective wire.

7. The manipulator according to claim 5, wherein the movable-gear means is configured such that each individual movable gear is provided in a movable manner so that engagement of one individual movable gear with at least one of the drive gear and a respective individual driven gear is released when the drive gear is rotated in a manner in which a respective pulley unwinds a respective wire.

8. The manipulator according to claim 5, further comprising a pair of movable pulleys, each individual movable pulley of the pair of movable pulleys being coaxially disposed at a respective individual movable gear,
wherein a respective individual wire passes over each individual movable pulley on opposite sides of, flanking shafts thereof, the positions at which each respective movable gear engages with at least one of the drive gear and a respective individual driven gear.

9. A wire driving device comprising:
first and second wires, one end of each being attached to a movable member, the first and second wires being configured to antagonistically drive the movable member;

first and second pulleys, an other end of the first wire being secured to the first pulley and an other end of the second wire being secured to the second pulley, the first wire being wound around the first pulley and the second wire being wound around the second pulley;

first and second driven gears, the first gear being coaxially secured to the first pulley and the second gear being coaxially secured to the second pulley;

a drive gear that is connected to a driving source that generates motive power;

first and second movable gears, the first movable gear being disposed between the drive gear and the first driven gear and the second movable gear being disposed between the drive gear and the second driven gear, the motive power of the driving source being transmitted from the drive gear to the first movable gear and from the first movable gear to the first driven gear and the motive power of the driving source being transmitted from the drive gear to the second movable gear and from the second movable gear to the second driven gear; and a movable-gear means for moving the first and second movable gears in a direction in which each of the first and second movable gears are engaged with the drive gear and a respective one of the first and second driven gears.

10. The wire driving device according to claim 9, wherein the movable-gear means is configured such that the first and second movable gears are each provided in a movable manner so that the first and second movable gears engage with the drive gear and the first and second movable gears each engage with the first and second driven gears, respectively, when the drive gear is rotated in a manner in which the first and second pulleys wind the first and second wires, respectively.

11. The wire driving device according to claim 9, wherein the movable-gear means is configured such that the first and second movable gears are each provided in a movable manner so that engagement of the first movable gear with at least one of the drive gear and the first driven gear is released when the drive gear is rotated in a manner in which the first pulley unwinds the first wire.

12. The wire driving device according to claim 9, further comprising first and second movable pulleys, each of the first and second movable pulleys being coaxially disposed at a respective one of the first and second movable gears, wherein the first and second individual wires pass over the first and second movable pulleys, respectively, on opposite sides of, flanking shafts thereof, the positions at which the first and second movable gears, respectively, engage with at least one of the drive gear and a respective first and second driven gear.

13. A manipulator comprising:

a wire driving device comprising:

first and second wires, one end of each being attached to a movable member, the first and second wires being configured to antagonistically drive the movable member;

first and second pulleys, an other end of the first wire being secured to the first pulley and an other end of the second wire being secured to the second pulley, the first wire being wound around the first pulley and the second wire being wound around the second pulley;

first and second driven gears, the first gear being coaxially secured to the first pulley and the second gear being coaxially secured to the second pulley;

a drive gear that is connected to a driving source that generates motive power;

first and second movable gears, the first movable gear being disposed between the drive gear and the first driven gear and the second movable gear being disposed between the drive gear and the second driven gear, the motive power of the driving source being transmitted from the drive gear to the first movable gear and from the first movable gear to the first driven gear and the motive power of the driving source being transmitted from the drive gear to the second movable gear and from the second movable gear to the second driven gear;

a movable-gear means for moving the first and second movable gears in a direction in which each of the first and second movable gears are engaged with the drive gear and a respective one of the first and second driven gears; and a joint that supports the movable member in a movable manner.

14. The manipulator according to claim 13, wherein the movable-gear means is configured such that the first and second movable gears are each provided in a movable manner so that the first and second movable gears are each provided in a movable manner so that the first and second movable gears engage with the drive gear and the first and second movable gears each engage with the first and second driven gears, respectively when the drive gear is rotated in a manner in which the first and second pulleys wind the first and second wires, respectively.

15. The manipulator according to claim 13, wherein the movable-gear means is configured such that the first and second movable gears are each provided in a movable manner so that engagement of the first movable gear with at least one of the drive gear and the first driven gear is released when the drive gear is rotated in a manner in which the first pulley unwinds the first wire.

16. The manipulator according to claim 13, further comprising first and second movable pulleys, each of the first and second movable pulleys being coaxially disposed at a respective one of the first and second movable gears, wherein the first and second individual wires pass over the first and second movable pulleys, respectively, on opposite sides of, flanking shafts thereof, the positions at which the first and second movable gears, respectively, engage with at least one of the drive gear and a respective first and second driven gear.

* * * * *